United States Patent [19]
McKenna et al.

[11] Patent Number: 5,511,544
[45] Date of Patent: Apr. 30, 1996

[54] NON-RESISTANT RESPIRATORY EXERCISER

[76] Inventors: Charles L. McKenna, 9744 1st St., Gerber, Calif. 96035; G. David Swanson, 2018 Burns Dr., Eureka, Calif. 95503

[21] Appl. No.: 376,903
[22] Filed: Jan. 23, 1995
[51] Int. Cl.⁶ ....................................................... A62B 7/00
[52] U.S. Cl. ............................... 128/205.13; 128/205.17; 128/204.18; 128/203.28
[58] Field of Search .......................... 128/205.25, 205.17, 128/205.13, 200.24, 200.22, 203.28, 203.29, 204.18

[56] References Cited

U.S. PATENT DOCUMENTS 4,854,574  8/1989  Larson et al. ...................... 128/200.24
5,217,006  6/1993  McCulloch ......................... 128/205.25

*Primary Examiner*—Ren Yan
*Assistant Examiner*—V. Srivastava

[57] ABSTRACT

A device for exercising respiratory muscles. By creating a cavity within its bottle like body, the device is able to trap a sufficient amount of exhaled $CO_2$, to prevent a subject from experiencing the effects of hyperventilation as the subject inhales and exhales at high and large respiratory rates and volumes respectively. The invention has at one end a face mask, which is fastened to a bottle like body. This bottle like body can be enlarged or reduced to create a varying size cavity that traps exhaled $CO_2$ and ambient air. An opening is placed at or near the bottom of the device that allows ambient air to enter the cavity. The opening is large enough so that no resistance of air flow is experienced during breathing exercise, as resistance of air flow may be damaging to lung tissue. The bottle like body which creates the cavity is divided into upper and lower halves. These halves slide or twist, one within the other to increase or decrease the size of the cavity, in order to accommodate differing lung capacities.

1 Claim, 1 Drawing Sheet

NON-RESISTANT RESPIRATORY EXERCISER

BACKGROUND OF INVENTION

1. Field of the Invention

This invention relates to exercise equipment used in exercising breathing muscles, with the present invention being particularly directed towards the exercising of the intercostal and diaphragm muscle found in air breathing mammals, particularly humans.

2. Description of the Prior Art

There is currently a device, U.S. Pat. No. 4,601,465 by Roy, July 1986, which is used for exercising breathing, however this device does this by creating a restrictive airflow, thus making a subject work harder while drawing air through it. Also there is currently a device, U.S. Pat. No. 4,037,595 which looks very much like the Non-Resistant Respiratory Exerciser as described herein, except that said prior art was designed and built expressly for pulmonary resuscitation, not pulmonary exercise.

SUMMARY OF INVENTION

Therefore, in practicing my invention I have provided a high volume, high respiratory rate lung muscle exerciser, that will maintain high levels of $CO_2$ within its cavity and at the same time allow ambient air to enter said cavity. With my device a rubber like face mask is attached to a plastic bottle like body at one end, at the other end of the bottle portion a hole is placed near its base, the bottle itself is divided into two halves, one half slides or twists into the other half so that the size of the cavity created by the two halves can either be increased or decreased to adjust for specific needs.

Therefore the principle object of the invention is to provide a respiratory exerciser that works by trapping the expelled $CO_2$ produced by the body during respiration and subsequently allowing that $CO_2$ to be rebreathed back into the lung cavity thus preventing hyperventilation during breathing exercises.

Other objects and advantages of the present invention will become understood by reading descriptions of numbered parts in the specifications and comparing the described parts with similarly number parts illustrated in the drawings.

DESCRIPTION OF THE PREFERRED EMBODIMENT

Figure 1:
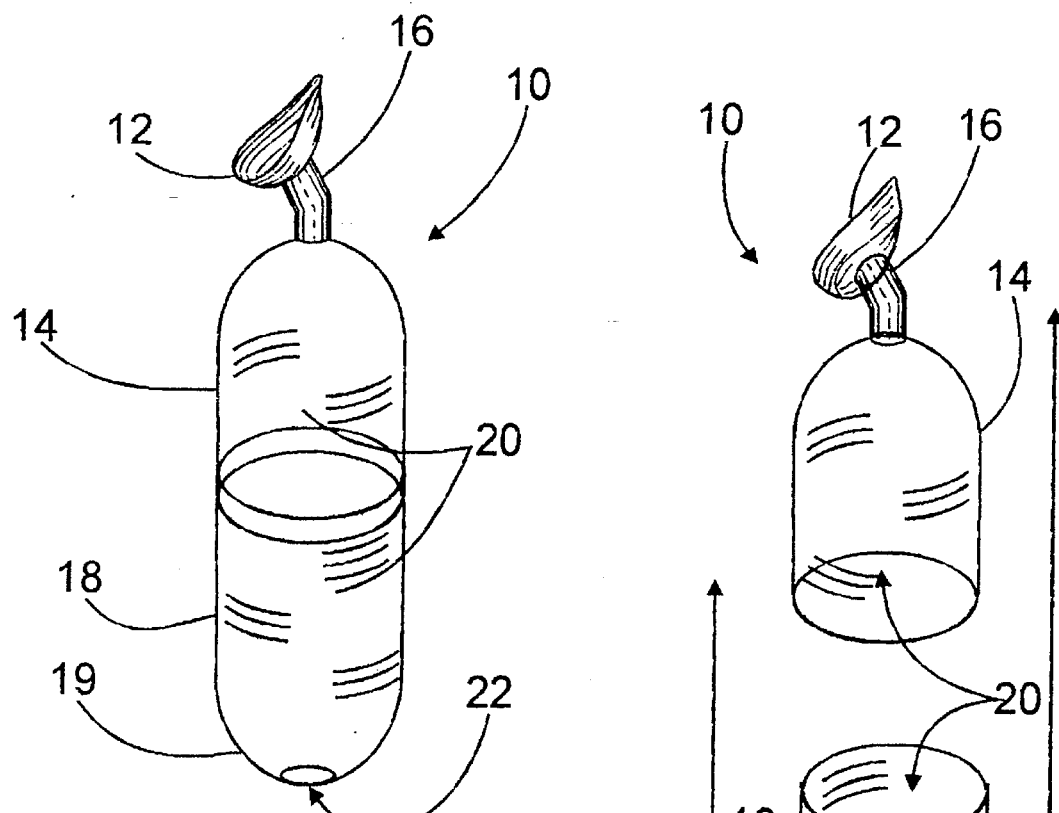
FIGS. 1 is a perspective illustration of the Non-Resistant Respiratory Exerciser.

Referring now to the drawings at FIG. 1, where the device 10, according to the invention, is illustrated. It is shown as a side view, at the top of the drawing is the face mask 12 portion of the invention. The face mask is made of a plastic or rubber like material which is large enough to cover a persons nose and mouth. The face mask 12 is attached to bottle like container 14 at the bottle's neck 16. The bottle 14 comprises an upper half 14 and a lower half 18. The upper half 14 and the lower half 18 are designed in such a manner as to allow the two halves to slide or twist one in the other, this sliding or twisting action can either increase or decrease the volume of the cavity 20 which is created by the two halves 14 and 18. Near the base 19 of lower half 18 is an opening 22, this opening allows ambient air to enter cavity 20 during inspiratory ventilations. Cavity 20 also traps $CO_2$ during expiratory ventilation.

Figure 2:
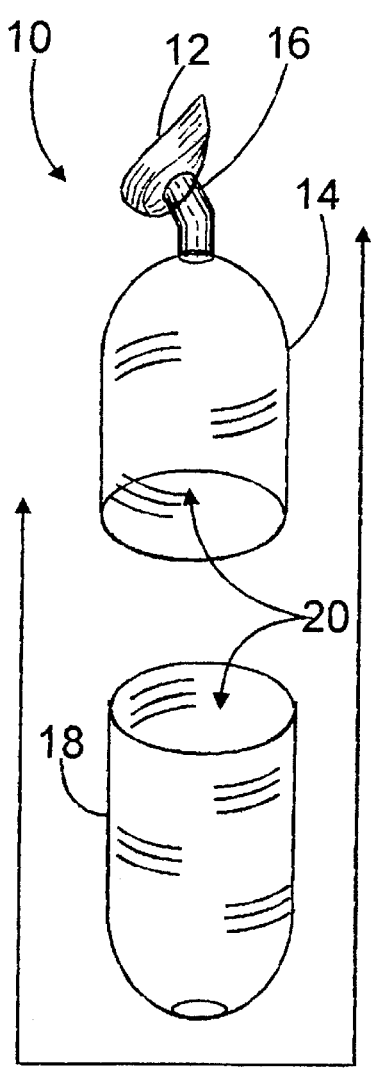
FIG. 2 is an exploded view showing the relationship of the two bottle like halves.

In referring to FIG. 2 showing an exploded view, the upper bottle 14 and the lower bottle 18 of FIG. 1 are separated.

Figure 3:
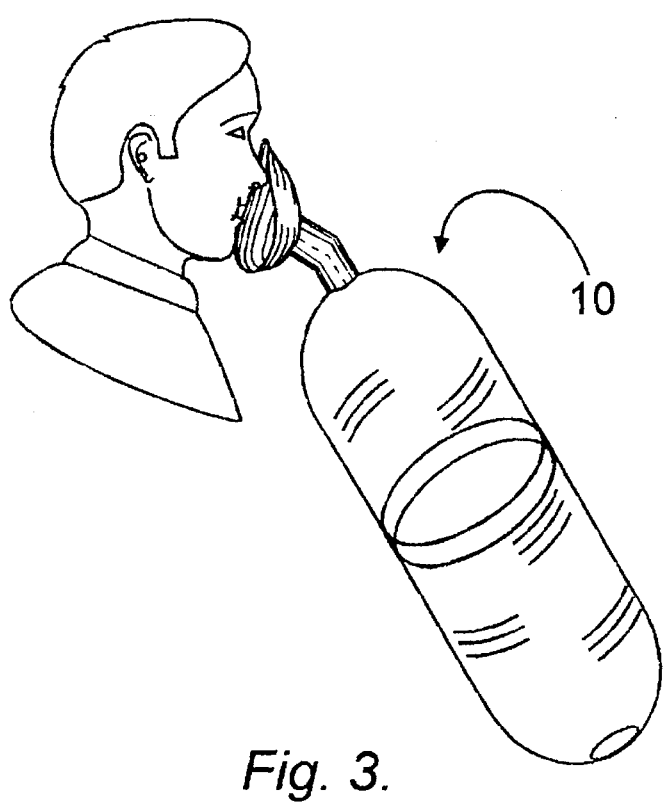
FIG. 3 shows the device attached to a subjects face.

In referring to FIG. 3 the device 10 is shown in its relationship to a subject, with face mask 12 coming in contact with the subjects face.

Although I have described an embodiment of my invention with considerable detail in the foregoing specification and have illustrated it extensively in the drawings, it is to be understood that I may practice variations in the invention which do not exceed the scope of the appended claims and that variations of my invention practiced by others which fall within the scope of my claims, I shall consider to be my invention.

What is claimed:

1. A respiratory exercising device consisting of a face mask, an enlarged cavity composed of first and second sections, each of said sections having a rounded end joined by a substantially cylindrical portion, a passageway extending from a first open end at said mask to a second open end substantially centrally located in the rounded end of said first section of said enlarged cavity, said first and second open ends being the only openings in said passageway, said passageway being unobstructed between said first and second open ends at all times, said substantially cylindrical portions of said first and second sections of said enlarged cavity being telescopically joined so that said enlarged cavity may be expanded or contracted by relative telescoping movement of said first and second sections, said second section having an aperture located substantially centrally therein in its rounded end to allow airflow into and out of said enlarged cavity.

* * * * *